(12) United States Patent
Wilson et al.

(10) Patent No.: US 10,449,339 B2
(45) Date of Patent: *Oct. 22, 2019

(54) CATHETER WITH STEPPED SKIVED HYPOTUBE

(71) Applicant: ABBOTT CARDIOVASCULAR SYSTEMS INC., Santa Clara, CA (US)

(72) Inventors: Bruce M. Wilson, Temecula, CA (US); Kerry J. Williams, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 393 days.

This patent is subject to a terminal disclaimer.

(21) Appl. No.: 15/449,462

(22) Filed: Mar. 3, 2017

(65) Prior Publication Data
US 2017/0173308 A1 Jun. 22, 2017

Related U.S. Application Data

(63) Continuation of application No. 14/458,327, filed on Aug. 13, 2014, now Pat. No. 9,616,198, which is a
(Continued)

(51) Int. Cl.
*A61M 25/10* (2013.01)
*A61M 25/00* (2006.01)
(Continued)

(52) U.S. Cl.
CPC ...... *A61M 25/104* (2013.01); *A61M 25/0009* (2013.01); *A61M 25/0026* (2013.01);
(Continued)

(58) Field of Classification Search
CPC .............. A61M 25/10; A61M 25/1002; A61M 2025/1004; A61M 25/1006;
(Continued)

(56) References Cited

U.S. PATENT DOCUMENTS 4,522,867 A 6/1985 Hill, Jr. et al.
4,782,834 A 11/1988 Maguire et al.
(Continued)

FOREIGN PATENT DOCUMENTS

EP 1 084 728 3/2001
EP 1 306 062 5/2003
(Continued)

OTHER PUBLICATIONS

U.S. Appl. No. 14/843,074, May 15, 2018 Applicant Initiated Interview Summary.
(Continued)

*Primary Examiner* — Wade Miles
(74) *Attorney, Agent, or Firm* — Baker Botts L.L.P.

(57) ABSTRACT

Catheter having a hypotube with a skive defined by a first angled cut, an axial cut, and a second angled cut. A midshaft member includes a guidewire lumen and an inflation lumen in fluid communication with an inflation lumen of the hypotube, the inflation lumen of the midshaft member configured to receive at least a portion of the hypotube. A distal tubular shaft member extends distally from the midshaft member. The distal tubular shaft member has a guidewire lumen and an inflation lumen defined therein, the guidewire lumen of the distal tubular shaft member in fluid communication with the guidewire lumen of the midshaft member. The inflation lumen of the distal tubular shaft member is in fluid communication with the inflation lumen of the midshaft member and a balloon is coupled to the distal tubular shaft member and in fluid communication with the inflation lumen.

34 Claims, 6 Drawing Sheets

Related U.S. Application Data continuation of application No. 13/481,441, filed on May 25, 2012, now Pat. No. 8,834,510.

(60) Provisional application No. 61/490,547, filed on May 26, 2011.

(51) Int. Cl.
   *A61M 25/01* (2006.01)
   *A61M 29/02* (2006.01)
   *B29C 55/22* (2006.01)
   *A61B 17/22* (2006.01)

(52) U.S. Cl.
   CPC .... *A61M 25/0028* (2013.01); *A61M 25/0052* (2013.01); *A61M 25/0054* (2013.01); *A61M 25/10* (2013.01); *B29C 55/22* (2013.01); *A61B 2017/22002* (2013.01); *A61M 2025/006* (2013.01); *A61M 2025/0183* (2013.01); *A61M 2029/025* (2013.01)

(58) Field of Classification Search
   CPC ...... A61M 25/1011; A61M 2025/1013; A61M 25/1018; A61M 2025/0023; A61M 2025/0024; A61M 25/0054; A61M 25/0026; A61M 2025/018; A61M 25/0029; A61F 2/958; A61F 2002/9583; A61F 2002/9586; A61F 2/2433; A61F 2/243; A61F 2/2427; A61F 2002/011
   See application file for complete search history.

(56) References Cited

U.S. PATENT DOCUMENTS

| | | |
|---|---|---|
| 4,976,690 A | 12/1990 | Solar et al. |
| 5,156,594 A | 10/1992 | Keith |
| 5,217,434 A | 6/1993 | Arney |
| 5,217,482 A | 6/1993 | Keith |
| 5,279,562 A | 1/1994 | Sirhan et al. |
| 5,370,616 A | 12/1994 | Keith et al. |
| 5,370,655 A | 12/1994 | Burns |
| 5,387,193 A | 2/1995 | Miraki |
| 5,387,225 A | 2/1995 | Euteneuer et al. |
| 5,395,334 A | 3/1995 | Keith et al. |
| 5,423,754 A | 6/1995 | Cornelius et al. |
| 5,458,615 A | 10/1995 | Klemm et al. |
| 5,490,837 A | 2/1996 | Blaeser et al. |
| 5,507,768 A | 4/1996 | Lau et al. |
| 5,522,818 A * | 6/1996 | Keith ................ A61M 25/0662 604/103.09 |
| 5,533,968 A | 7/1996 | Muni et al. |
| 5,643,209 A | 7/1997 | Fugoso et al. |
| 5,649,909 A | 7/1997 | Cornelius |
| 5,743,875 A | 4/1998 | Sirhan et al. |
| 5,833,706 A | 11/1998 | St Germain et al. |
| 5,908,406 A | 6/1999 | Ostapchenko et al. |
| 6,083,232 A | 7/2000 | Cox |
| 6,102,890 A | 8/2000 | Stivland et al. |
| 6,217,547 B1 | 4/2001 | Lee |
| 6,277,093 B1 | 8/2001 | Lee |
| 6,575,958 B1 | 6/2003 | Happ et al. |
| 6,620,127 B2 | 9/2003 | Lee et al. |
| 6,695,812 B2 | 2/2004 | Estrada et al. |
| 6,702,802 B1 | 3/2004 | Hancock et al. |
| 6,746,423 B1 | 6/2004 | Wantink |
| 6,887,219 B2 * | 5/2005 | Wantink ............ A61M 25/0052 604/103.04 |
| 6,890,318 B2 * | 5/2005 | Wantink ............ A61M 25/0052 604/103.04 |
| 6,923,822 B2 | 8/2005 | Crawford et al. |
| 6,964,750 B2 | 11/2005 | Fulford |
| 7,001,420 B2 | 2/2006 | Speck et al. |
| 7,074,206 B2 | 7/2006 | Lee et al. |
| 7,195,611 B1 | 3/2007 | Simpson et al. |
| 7,273,470 B2 * | 9/2007 | Wantink ............ A61M 25/0052 604/103.04 |
| 7,303,798 B2 | 12/2007 | Bavaro et al. |
| 7,322,959 B2 | 1/2008 | Warnack et al. |
| 7,549,975 B2 | 6/2009 | Lee et al. |
| 7,828,766 B2 | 11/2010 | Durcan |
| 7,833,597 B2 | 11/2010 | Bavaro et al. |
| 7,862,541 B2 | 1/2011 | Jeffrey et al. |
| 7,906,066 B2 | 3/2011 | Wilson et al. |
| 7,951,259 B2 | 5/2011 | Duchamp et al. |
| 7,967,781 B2 | 6/2011 | Simpson et al. |
| 7,967,836 B2 | 6/2011 | Warnack et al. |
| 8,048,058 B2 | 11/2011 | Fulford |
| 8,052,638 B2 | 11/2011 | Lee et al. |
| 8,057,430 B2 | 11/2011 | Grovender et al. |
| 8,251,949 B2 | 8/2012 | Wamack |
| 8,382,738 B2 | 2/2013 | Simpson et al. |
| 8,382,935 B2 * | 2/2013 | Simpson ............ A61M 25/0023 156/211 |
| 8,394,055 B2 | 3/2013 | Durcan |
| 8,444,608 B2 | 5/2013 | Haslinger et al. |
| 8,444,802 B2 | 5/2013 | Lee et al. |
| 8,637,132 B2 | 1/2014 | Bavaro et al. |
| 8,834,510 B2 | 9/2014 | Wilson et al. |
| 8,840,743 B2 | 9/2014 | Wantink et al. |
| 9,132,259 B2 | 9/2015 | Lin et al. |
| 2002/0072705 A1 | 6/2002 | Vrba et al. |
| 2003/0125709 A1 | 7/2003 | Eidenschink |
| 2003/0135231 A1 | 7/2003 | Goodin et al. |
| 2004/0082935 A1 | 4/2004 | Lee et al. |
| 2005/0070847 A1 | 3/2005 | van Erp et al. |
| 2005/0261725 A1 | 11/2005 | Crawford et al. |
| 2006/0135909 A1 | 6/2006 | Holman et al. |
| 2007/0021772 A1 | 1/2007 | von Oepen et al. |
| 2007/0173919 A1 | 7/2007 | Maschke |
| 2008/0015499 A1 | 1/2008 | Warnack |
| 2008/0077085 A1 | 3/2008 | Eidenschink et al. |
| 2008/0125707 A1 | 5/2008 | Wilson et al. |
| 2009/0036829 A1 | 2/2009 | Pagel et al. |
| 2009/0171281 A1 | 7/2009 | Pipenhagen et al. |
| 2009/0223624 A1 | 9/2009 | Lee et al. |
| 2010/0130925 A1 | 5/2010 | Haslinger et al. |
| 2010/0189876 A1 | 7/2010 | Kokish et al. |
| 2010/0217234 A1 | 8/2010 | Grovender et al. |
| 2010/0285085 A1 | 11/2010 | Stankus et al. |
| 2011/0022150 A1 | 1/2011 | Durcan |
| 2011/0060276 A1 | 3/2011 | Schaeffer et al. |
| 2011/0070355 A1 | 3/2011 | Bavaro et al. |
| 2011/0160834 A1 | 6/2011 | Aggerholm |
| 2011/0172696 A1 | 7/2011 | Jeffrey et al. |
| 2012/0065718 A1 | 3/2012 | Simpson et al. |
| 2012/0226229 A1 | 9/2012 | Watanabe et al. |
| 2012/0302952 A1 | 11/2012 | Kitada et al. |
| 2012/0302994 A1 | 11/2012 | Wilson et al. |
| 2012/0303054 A1 | 11/2012 | Wilson et al. |
| 2013/0178795 A1 | 7/2013 | Wilson et al. |
| 2014/0276401 A1 | 9/2014 | Lee et al. |

FOREIGN PATENT DOCUMENTS

| | | |
|---|---|---|
| JP | 2001-333984 A | 12/2001 |
| JP | 2008-237844 A | 10/2008 |
| JP | 2010-220760 A | 10/2010 |
| JP | 6-114109 B2 | 4/2017 |
| WO | WO 01/43944 A1 | 6/2001 |
| WO | WO 03/037418 A2 | 5/2003 |
| WO | WO 2008/005706 A2 | 1/2008 |
| WO | WO 2012/042619 A1 | 4/2012 |
| WO | WO 2012/162651 A1 | 11/2012 |

OTHER PUBLICATIONS

U.S. Appl. No. 14/843,249, May 18, 2018 Applicant Initiated Interview Summary.
U.S. Appl. No. 14/843,249, May 8, 2018 Response after Final Action.

(56) References Cited

OTHER PUBLICATIONS

U.S. Appl. No. 14/843,308, May 17, 2018 Amendment and Request for Continued Examination (RCE).
U.S. Appl. No. 14/843,308, May 15, 2018 Applicant Initiated Interview Summary.
U.S. Appl. No. 14/843,308, May 1, 2018 Advisory Action.
U.S. Appl. No. 14/843,308, Apr. 12, 2018 Response after Final Action.
U.S. Appl. No. 14/843,372, May 16, 2018 Applicant Initiated Interview Summary.
U.S. Appl. No. 13/481,441 (U.S. Pat. No. 8,834,510), filed May 25, 2012 (Sep. 16, 2014).
U.S. Appl. No. 14/458,327 (U.S. Pat. No. 9,616,198), filed Aug. 13, 2014 (Apr. 11, 2017).
U.S. Appl. No. 14/843,249 (US 2016/0067458), filed Sep. 2, 2015 (Mar. 10, 2016).
U.S. Appl. No. 14/843,308 (US 2016/0339204), filed Sep. 2, 2015 (Nov. 24, 2016).
U.S. Appl. No. 14/843,372 (US 2016/0067459), filed Sep. 2, 2015 (Mar. 10, 2016).
U.S. Appl. No. 13/481,441, Aug. 13, 2014 Issue Fee payment.
U.S. Appl. No. 13/481,441, Jun. 18, 2014 Notice of Allowance.
U.S. Appl. No. 13/481,441, Apr. 18, 2014 Response to Non-Final Office Action.
U.S. Appl. No. 13/481,441, Dec. 18, 2013 Non-Final Office Action.
U.S. Appl. No. 13/481,441, Sep. 12, 2013 Response to Restriction Requirement.
U.S. Appl. No. 13/481,441, Aug. 15, 2013 Restriction Requirement.
U.S. Appl. No. 14/458,327, Mar. 3, 2017 Issue Fee Payment.
U.S. Appl. No. 14/458,327, Dec. 5, 2016 Notice of Allowance.
U.S. Appl. No. 14/458,327, Nov. 14, 2016 Response to Restriction Requirement.
U.S. Appl. No. 14/458,327, Sep. 13, 2016 Restriction Requirement.
U.S. Appl. No. 14/843,308, Apr. 4, 2017 Non-Final Office Action.
U.S. Appl. No. 14/843,372, Apr. 4, 2017 Non-Final Office Action.
European Search Report dated Jan. 29, 2016 in EP Application No. 15183531.
European Search Report dated Oct. 13, 2016 in Application No. EP 15183533.
European Search Report dated Oct. 14, 2016 in Application No. EP 15183534.
U.S. Appl. No. 14/843,074 (US 2016/0339211), filed Sep. 2, 2015 (Nov. 24, 2016).
U.S. Appl. No. 14/843,074, Jun. 5, 2017 Non-Final Office Action.
U.S. Appl. No. 14/843,249, Jul. 12, 2017 Non-Final Office Action.
U.S. Appl. No. 14/843,308, Aug. 4, 2017 Response to Non-Final Office Action.
U.S. Appl. No. 14/843,372, Aug. 4, 2017 Response to Non-Final Office Action.
U.S. Appl. No. 14/843,249, Nov. 21, 2017 Final Office Action.
U.S. Appl. No. 14/843,249, Oct. 12, 2017 Response to Non-Final Office Action.
U.S. Appl. No. 14/843,308, Nov. 17, 2017 Final Office Action.
U.S. Appl. No. 14/843,372, Nov. 21, 2017 Final Office Action.
U.S. Appl. No. 14/843,074, Nov. 22, 2017 Final Office Action.
U.S. Appl. No. 14/843,074, Oct. 5, 2017 Response to Non-Final Office Action.
International Search Report for PCT/US2012/039678, dated Sep. 21, 2012 (Corresponds to U.S. Appl. No. 13/481,441).
Partial European Search Report dated Jan. 29, 2016 in EP Application No. 15183539.

* cited by examiner

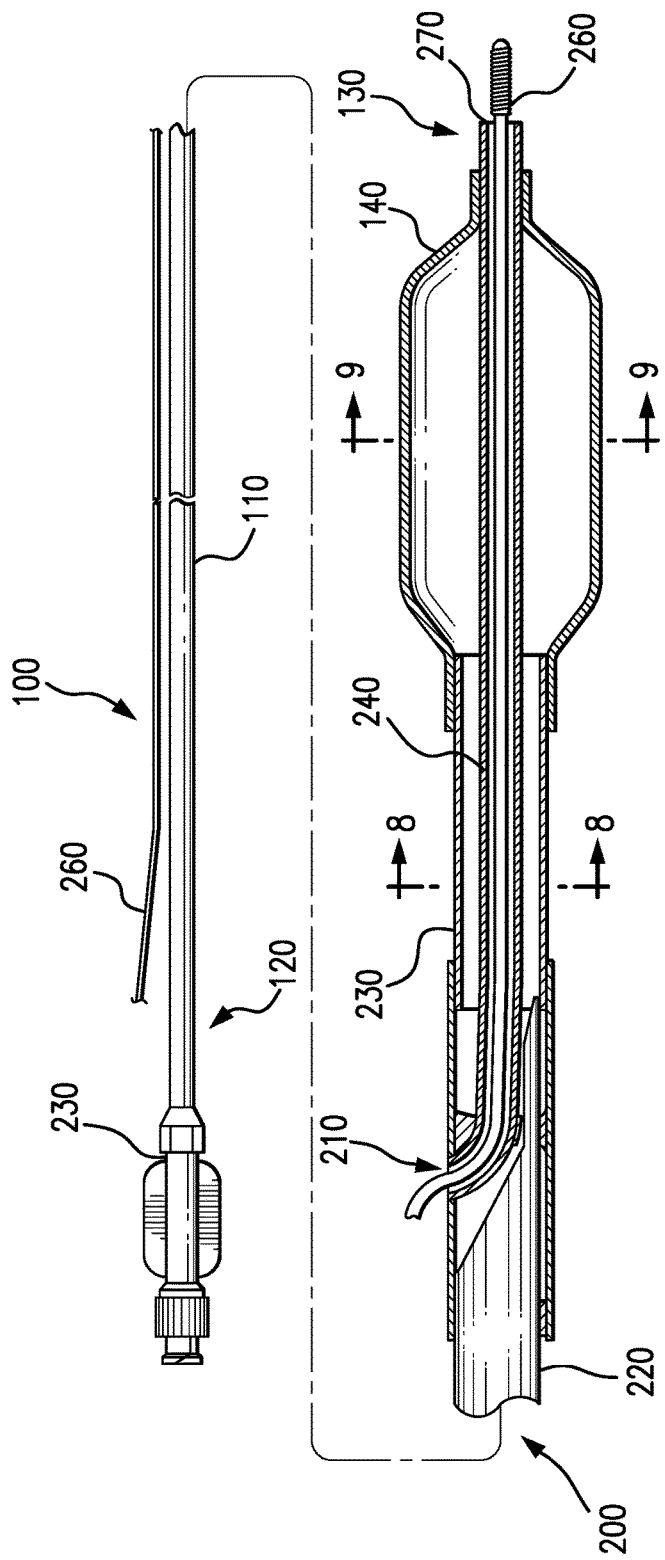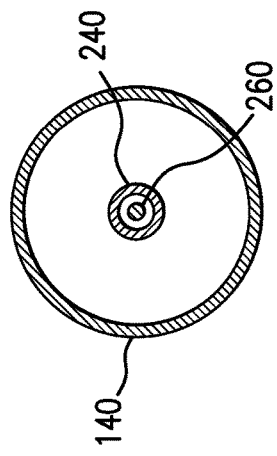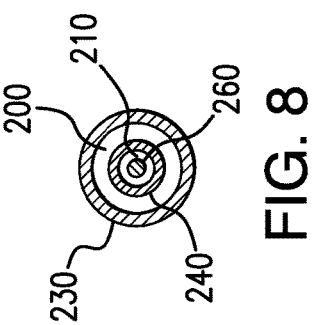
FIG. 1
FIG. 8
FIG. 9

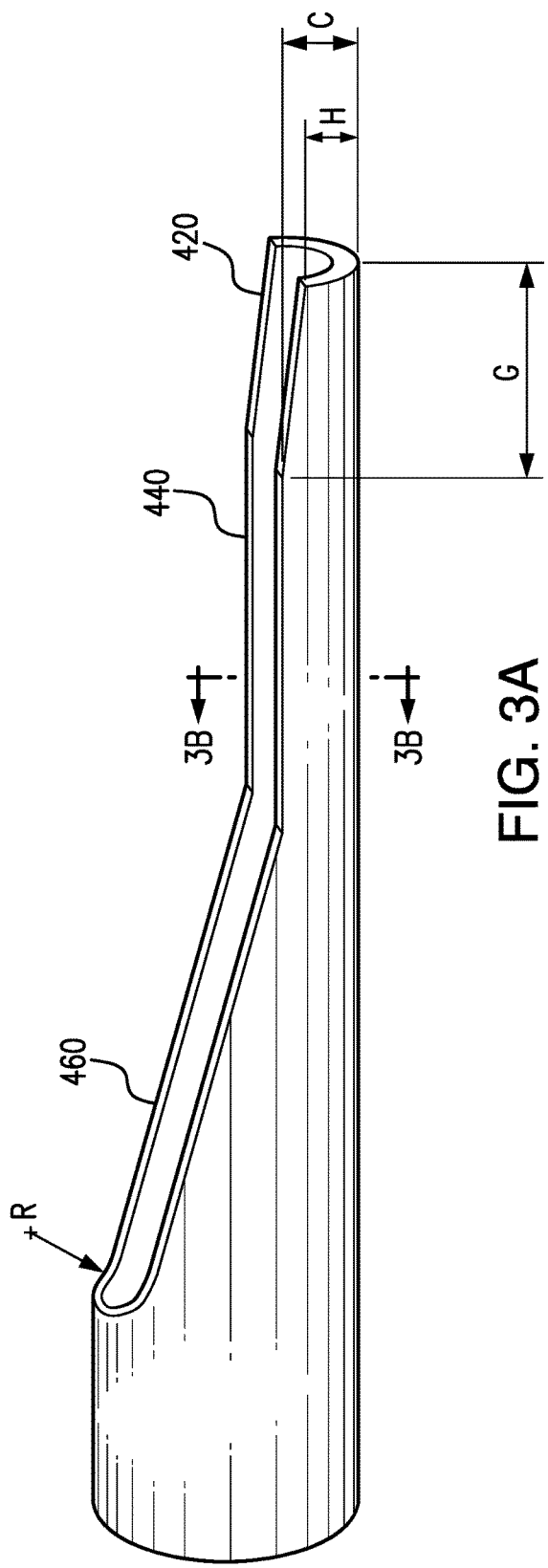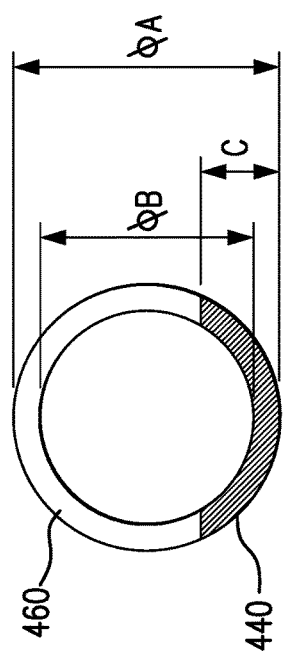
FIG. 3A
FIG. 3B

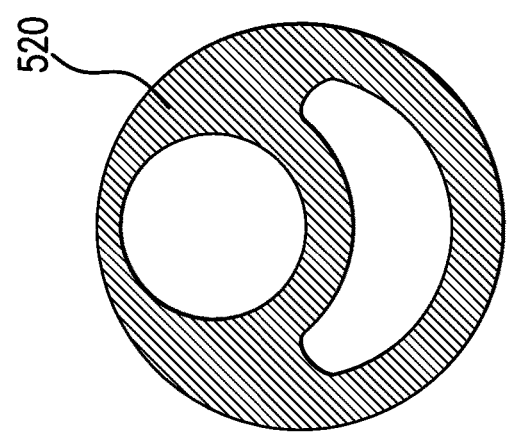
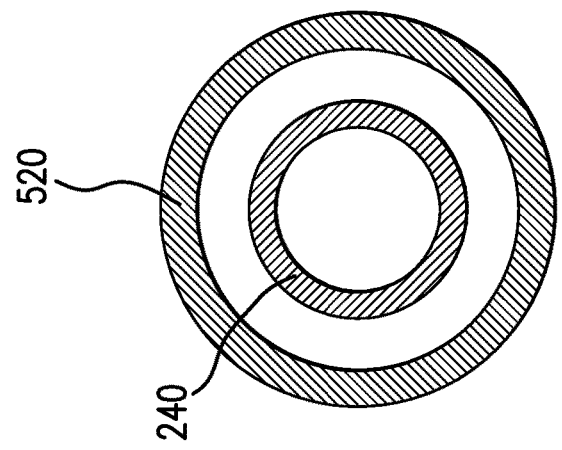

CATHETER WITH STEPPED SKIVED HYPOTUBE

CROSS-REFERENCE TO RELATED APPLICATION

This application is a continuation of U.S. patent application Ser. No. 14/458,327, filed Aug. 13, 2014, which is a continuation of U.S. patent application Ser. No. 13/481,441, filed May 25, 2012, now U.S. Pat. No. 8,834,510 issued Sep. 16, 2014, which claims the benefit of U.S. Provisional Patent Application Ser. No. 61/490,547, entitled "Catheter With Stepped Skived Hypotube" and filed on May 26, 2011, the entire content of each of which is incorporated herein by reference.

BACKGROUND OF THE DISCLOSED SUBJECT MATTER

Field of the Disclosed Subject Matter

The disclosed subject matter herein generally relates to medical devices, and particularly to intracorporeal devices for therapeutic or diagnostic uses, such as balloon catheters.

DESCRIPTION OF RELATED SUBJECT MATTER

In percutaneous transluminal coronary angioplasty (PTCA) procedures, a guiding catheter is advanced in the vasculature of a patient until the distal tip of the guiding catheter is seated in a desired coronary artery. A guidewire is advanced out of the distal end of the guiding catheter into the coronary artery until the distal end of the guidewire crosses a lesion to be dilated. A dilatation catheter, having an inflatable balloon on the distal portion thereof, is advanced into the coronary anatomy over the previously introduced guidewire until the balloon of the dilatation catheter is positioned across the lesion. Once positioned, the dilatation balloon is inflated with inflation fluid one or more times to a predetermined size at a suitable pressure to compress the stenosis against the arterial wall to open up the vascular passageway. Generally, the inflated diameter of the balloon is approximately the same diameter as the native diameter of the body lumen being dilated to complete the dilatation but not over expand the artery wall. After the balloon is deflated, blood resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians may additionally or alternatively implant an intravascular prosthesis inside the artery at the site of the lesion. Such stents may be bare metal, polymeric, or coated with a drug or other therapeutic agent. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter with the stent implanted within the artery at the site of the dilated lesion. Coverings on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together. For details of example stents, see for example, U.S. Pat. No. 5,507,768 (Lau, et al.) and U.S. Pat. No. 5,458,615 (Klemm, et al.), which are incorporated herein by reference.

In addition to PTA, PTCA, and atherectomy procedures, balloon catheters are also used to the peripheral system such as in the veins system or the like. For instance, a balloon catheter is initially advanced over a guidewire to position the balloon adjacent a stenotic lesion. Once in place, the balloon is then inflated, and the restriction of the vessel is opened. Likewise, balloon catheters are also used for treatment of other luminal systems throughout the body.

Typically, balloon catheters comprise a hollow catheter shaft with a balloon secured at a distal end. The interior of the balloon is in a fluid flow relation with an inflation lumen extending along a length of the shaft. Fluid under pressure can thereby be supplied to the interior of the balloon through the inflation lumen. To position the balloon at the stenosed region, the catheter shaft is designed to have suitable pushability (i.e., ability to transmit force along the length of the catheter), trackability, and flexibility, to be readily advanceable within the tortuous anatomy of the vasculature. Conventional balloon catheters for intravascular procedures, such as angioplasty and stent delivery, frequently have a relatively stiff proximal shaft section to facilitate advancement of the catheter within the body lumen and a relatively flexible distal shaft section to facilitate passage through tortuous anatomy, such as distal coronary and neurological arteries, without damage to the vessel wall.

Traditional catheter shafts are often constructed with inner and outer member tubing separately with an annular space therebetween for balloon inflation. In the design of catheter shafts, it is desirable to predetermine or control characteristics such as strength, stiffness and flexibility of various sections of the catheter shaft to provide the desired catheter performance. This is conventionally performed by combining separate lengths of tubular members of different material and/or dimensions and then assembling the separate members into a single shaft length. However, the transition between sections of different stiffness or material can be a cause of undesirable kinking along the length of the catheter. Such kinking is particularly evident in rapid exchange (RX) catheters, wherein the proximal shaft section does not include the additional structure of a guidewire lumen tube. For example, a conventional RX catheter generally consists of a proximal hypotube having a single inflation lumen therethrough and a dual lumen or coaxial tube configuration at a distal end section having both a guidewire lumen and an inflation lumen therein. Known techniques to minimize kinking at the transition between the more rigid proximal section and the more flexible distal section include bonding two or more segments of different flexibility together to form the shaft. Such transition bonds need to be sufficiently strong to withstand the pulling and pushing forces on the shaft during use.

To address the described issues, catheters having varied flexibility and/or stiffness have been developed with various sections of the catheter shaft that are specifically tailored to provide the desired catheter performance. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; U.S. Pat. No. 5,649,909 to Cornelius discloses a catheter having a proximal portion with greater stiffness due to the application of a polymeric coating thereto; and U.S. Publication No. 2010/0130925 to Haslinger discloses a multilayer catheter shaft using a combination of a high Shore D durometer value material and a lower Shore D durometer value material to reduce kinking.

However, one difficulty has been balancing the often competing characteristics of strength and flexibility of the catheter shaft. The transition between sections of different stiffness or material can be a cause of undesirable kinking along the length of the catheter. Such kinking is particularly evident in rapid exchange catheters, wherein the proximal shaft section does not include the additional structure of a guidewire lumen tube. Rather, a conventional rapid exchange catheter generally consists at its proximal end section of a covered hypotube having a single inflation lumen therethrough and at its distal end section, a dual lumen or coaxial tube configuration having both a guidewire lumen and an inflation lumen therein. Known techniques to minimize kinking at the transition between the more rigid proximal section and the more flexible distal section include bonding two or more segments of different flexibility together to form the shaft. However, such transition bonds need to be sufficiently strong to withstand the pulling and pushing forces on the shaft during use. One difficultly has been providing a flexibility transition which improves catheter maneuverability, yet with a sufficiently strong transition bond.

Accordingly, there is a need for a catheter having a catheter shaft with an improved combination of characteristics such as strength, flexibility and ease of manufacture. The disclosed subject matter satisfies these and other needs.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve the above and other advantages and in accordance with the purpose of the disclosed subject matter, as embodied and broadly described, the disclosed subject matter includes, according to one embodiment, a catheter comprising a hypotube having a proximal section and a distal section with an inflation lumen and a longitudinal axis defined therethrough, the distal section having a skive defined by a first angled cut, an axial cut, and a second angled cut. The catheter further has a midshaft member including a guidewire lumen and an inflation lumen defined therethrough, the inflation lumen of the midshaft member in fluid communication with the inflation lumen of the hypotube. The inflation lumen of the midshaft member is configured to receive at least a portion of the distal section of the hypotube. The catheter further has a distal tubular shaft member extending distally from the midshaft member, the distal tubular shaft member having a guidewire lumen and an inflation lumen defined therein, the guidewire lumen of the distal tubular shaft member in fluid communication with the guidewire lumen of the midshaft member. The inflation lumen of the distal tubular shaft member is in fluid communication with the inflation lumen of the midshaft member. The catheter further has a balloon coupled to the distal tubular shaft member and in fluid communication with the inflation lumen.

In accordance with another aspect of the disclosed subject matter, the hypotube of the proximal section is free of any outer coating or layer. In this manner, the hypotube can be dimensioned to match the corresponding outer diameter of a coated hypotube of a conventional catheter. Similarly, the inner diameter is increased while maintaining suitable strength and rigidity. This bare hypotube configuration allows for increased rigidity and pushability, as well as increased flow rates through the inflation lumen for inflation and/or deflation as desired, without jeopardizing overall profile. The distal section of the bare hypotube is textured, such as by laser treatment, to increase adhesion with the midshaft section tube.

The distal end of the hypotube can be roughened or textured to improve adhesion of the hypotube with the middle section shaft as described further below. For example, a laser can treat the end of the hypotube for enhanced adhesion.

A catheter of the disclosed subject matter has an improved transition, such as a flexibility transition along a length of the catheter shaft which preferably provides improved trackability. These and other advantages of the disclosed subject matter will become more apparent from the following detailed description and accompanying exemplary drawings.

In accordance with another aspect of the disclosed subject matter, a method of making a catheter is disclosed including providing a hypotube having a proximal section and a distal section with an inflation lumen and a longitudinal axis defined therethrough, the distal section having a skive defined by a first angled cut, an axial cut, and a second angled cut. The method further includes forming a midshaft member including a guidewire lumen and an inflation lumen defined therethrough, the inflation lumen of the midshaft member configured to receive at least a portion of the distal section of the hypotube. The distal section of the hypotube is inserted within the midshaft member with at least the axial cut of the skive engaging the inflation lumen of the midshaft member and the inflation lumen of the midshaft member in fluid communication with the inflation lumen of the hypotube. The midshaft member is bonded to an outer surface of the hypotube.

It is to be understood that both the foregoing general description and the following detailed description are embodiments and are intended to provide further explanation of the disclosed subject matter claimed. The accompanying drawings, which are incorporated in and constitute part of this specification, are included to illustrate and provide a further understanding of the system and method of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 1 is a side view, partially in section, of a balloon catheter embodying features of the disclosed subject matter.

FIG. 3A is a detail perspective view of the skive at the distal section of the hypotube according to an embodiment of the disclosed subject matter.

FIG. 3B is a cross section of the hypotube at section B-B in FIG. 3A according to an embodiment of the disclosed subject matter.

FIGS. 8 and 9 are transverse cross sectional views of the balloon catheter shown in FIG. 1, taken along lines 8-8 and 9-9, respectively.

FIGS. 10A and 10B are selected images of the cross section of the distal shaft section and the midshaft section according the disclosed subject matter.

DETAILED DESCRIPTION

Figure 2:
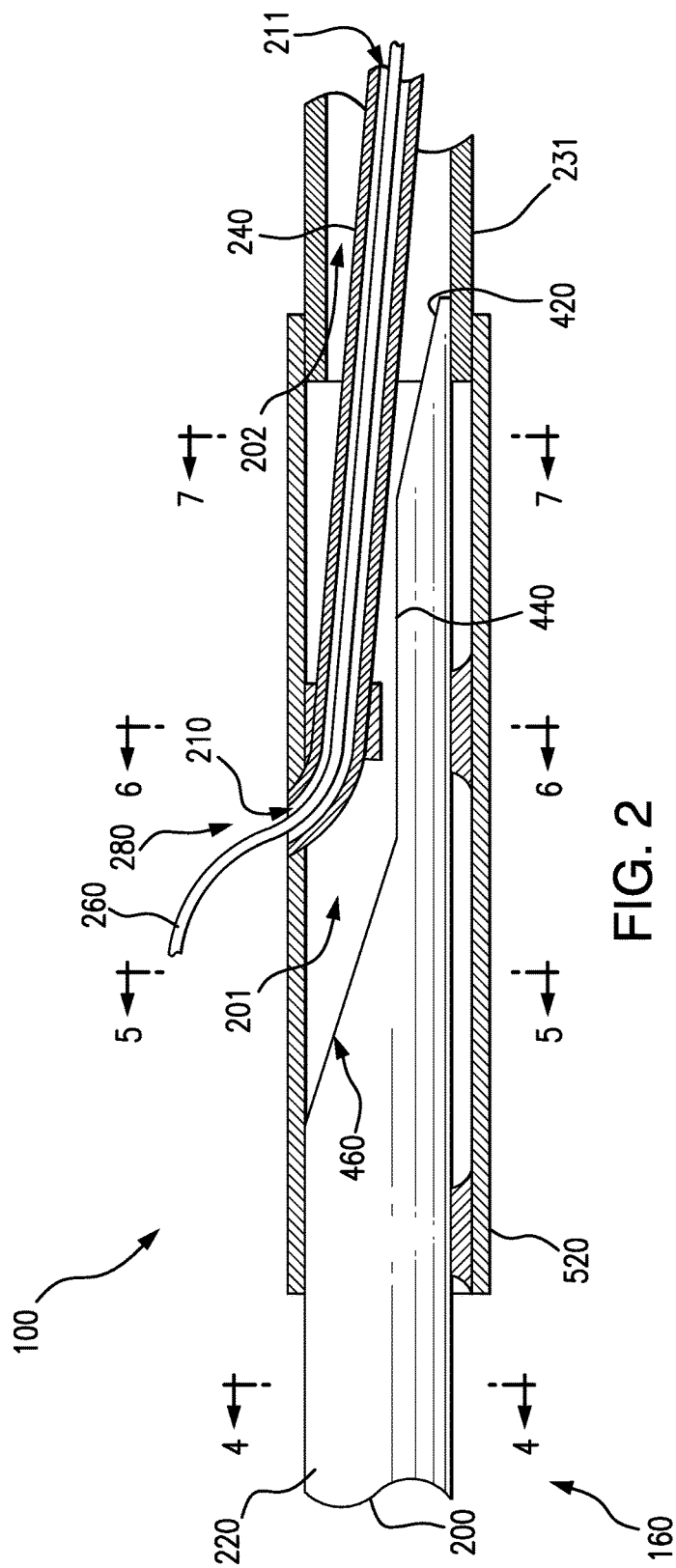
FIG. 2 is a detailed side cross section of the transition region, including the skived distal end of the catheter hypotube disposed within the inflation lumen of a midshaft section and extending into a portion of the inflation lumen of the distal shaft member.

Reference will now be made in detail to embodiments of the disclosed subject matter, an example of which is illustrated in the accompanying drawings. The examples are not intended to limit the scope of the disclosed subject matter in any manner. The disclosed subject matter will be described in conjunction with the detailed description of the system.

In accordance with an embodiment of the disclosed subject matter, a catheter comprising a hypotube having a proximal section and a distal section with an inflation lumen and a longitudinal axis defined therethrough, the distal section having a skive defined by a first angled cut, an axial cut, and a second angled cut. The catheter further has a midshaft member including a guidewire lumen and an inflation lumen defined therethrough, the inflation lumen of the midshaft member in fluid communication with the inflation lumen of the hypotube. The inflation lumen of the midshaft member is configured to receive at least a portion of the distal section of the hypotube. The catheter further has a distal tubular shaft member extending distally from the midshaft member is further provided, the distal tubular shaft member having a guidewire lumen and an inflation lumen defined therein, the guidewire lumen of the distal tubular shaft member in fluid communication with the guidewire lumen of the midshaft member. The inflation lumen of the distal tubular shaft member is in fluid communication with the inflation lumen of the midshaft member. The catheter further has a balloon coupled to the distal tubular shaft member and in fluid communication with the inflation lumen.

In accordance with another aspect of the disclosed subject matter, a method of making a catheter is disclosed including providing a hypotube having a proximal section and a distal section with an inflation lumen and a longitudinal axis defined therethrough, the distal section having a skive defined by a first angled cut, an axial cut, and a second angled cut. The method further includes forming a midshaft member including a guidewire lumen and an inflation lumen defined therethrough, the inflation lumen of the midshaft member configured to receive at least a portion of the distal section of the hypotube. The distal section of the hypotube is inserted within the midshaft member with at least the axial cut of the skive engaging the inflation lumen of the midshaft member and the inflation lumen of the midshaft member in fluid communication with the inflation lumen of the hypotube. The midshaft member is bonded to an outer surface of the hypotube.

For purpose of illustration and not limitation, reference will now be made in detail to specific embodiments, examples of which are illustrated in the accompanying drawings. For the purposes of this disclosure, like reference numbers in the figures shall refer to like features unless otherwise indicated. For purpose of illustration and not limitation, and unless otherwise noted, reference to dimensions and materials of construction will be made to a coronary balloon dilatation catheter, although it is recognized that alternative dimensions and materials of construction can be used for other indications.

Solely for purpose of illustration, an exemplary embodiment of a rapid exchange type balloon dilatation catheter 100 for coronary indications embodying features of the disclosed subject matter is shown in FIG. 1. The catheter 100 generally comprises an elongated catheter shaft 110 having a proximal shaft portion 120 and a distal shaft portion 130. The catheter shaft 110 can have a variety of suitable configurations. For example, although depicted as multiple tubes joined together, as discussed herein, certain portions can be formed as single monolithic members as desired. The shaft 110 has an inflation lumen 200 defined therein and a guidewire lumen 210 defined through at least a portion of the distal shaft section.

In accordance with one aspect of the disclosed subject matter as illustrated in FIG. 1, the proximal shaft section embodied herein is a single lumen hypotube 220 or similar tubular member of suitable rigidity and pushability. The hypotube 220 is embodied as a single piece construction tubular member. The hypotube 220 has a proximal section and a distal section with an inflation lumen 200 and a longitudinal axis defined therethrough. The inflation lumen 200 of the hypotube can comprise any suitable configuration, such as a substantially circular configuration as embodied in FIG. 1. For purpose of illustration, the substantially circular hypotube of FIG. 1 can have a wall thickness of between about 0.0030 inches and about 0.0090 inches when used for coronary indications. The distal section of the hypotube has a skive defined by a first angled cut, an axial cut, and a second angled cut, as further discussed herein.

In the illustrated embodiment of FIG. 1 and FIG. 2, the hypotube 220 is skived at its distal section with a stepped configuration. The skive is a cut section of the hypotube that gradually reduces in dimension. The stepped skive improves pushability and resistance to kink by providing a smoother transition between the hypotube and a midshaft member, further discussed herein.

As depicted in FIG. 2, the skive of the disclosed subject matter has three distinct sections comprising a first angled cut 420, an axial cut 440, and a second angled cut 460 and the hypotube reduces in cross-sectional dimension distally along the skive. The first angled cut 420 is at the extreme distal end of the hypotube and the axial cut 440 is disposed between the first angled cut 420 and the second angled cut 460. The first angled cut 420 extends to a distal end of the hypotube 220. For example, the hypotube in the first angled cut 420 can come to a point at the extreme distal end as depicted in FIG. 2, and in other embodiments, the distal end of the hypotube includes a blunt end as depicted in FIG. 3A for purpose of comparison. Other similar stepped configurations are contemplated.

The first angled cut 420 and second angled cut 460 each can have a linear or straight angled configuration as depicted herein, or can be curved, such as a parabolic like curve. The first angled cut 420 and the second angled cut 460 can have the same angle of inclination or can have different angles of inclination. In one embodiment as depicted in FIG. 2 for purposes of illustration, the first angled cut 420 and the second angled cut 460 are substantially parallel with each other. In another embodiment, the first angled cut 420 extends at a first angle relative the longitudinal axis of the hypotube and the second angled 460 cut extends at a second angle relative the longitudinal axis of the hypotube such that the first angle is different from the second angle.

The first angled cut 420, the axial cut 440, and the second angled cut 460 can have the same or varying lengths, although the overall dimensions will correspond with dimensions of the midshaft member as described further below. FIGS. 3A and 3B depict a schematic of the distal section of the hypotube 220 for a coronary balloon dilation catheter, wherein the hypotube has the first angled cut 420, the axial cut 440, and the second angled cut 460. In the example of FIGS. 3A and 3B, the first angled cut 420 has an axial length G between approximately between about 20 mm and about 30 mm. The first angled cut 420 of this embodiment has a blunt end which can have a distal height H ranging approximately between approximately 5% to approximately 25% of the outer diameter of the hypotube 220. In one embodiment, the height H can be approximately 0.0025 inches to approximately 0.0065 inches.

The axial cut 440 can have an axial length approximately ranging between 10 mm and 40 mm. The axial cut 440 can have a height C, as depicted in FIG. 3A, that ranges approximately between about 20% to about 50% of the outer diameter of the hypotube 220. In one embodiment, the height C ranges between about 0.0060 inches and about 0.0110 inches.

FIG. 3B is a cross-section of FIG. 3A along the lines B-B. FIG. 3B depicts the outside diameter $\varnothing_A$ and the inside diameter $\varnothing_B$. In one embodiment, the inside diameter $\varnothing_B$ of the hypotube 220 can be approximately 0.0200 inches to approximately 0.0220 inches and the outside diameter $\varnothing_A$ of the hypotube 220 can be approximately 0.0260 inches to approximately 0.0280 inches. The second angled cut 460 can have a height approximately equivalent to the outside diameter of the hypotube 220. Accordingly, in one embodiment, the second angled cut has an overall height when measured from a side of between about 50% to approximately 100% of the outer diameter of the hypotube 220. FIG. 3B further depicts the height C of the axial cut 440 in relation to the outside diameter $\varnothing_A$ and the inside diameter $\varnothing_B$.

Additionally, an end of one or more cuts can be radiused for transition purposes. For example, and as depicted in FIG. 3A, a proximal end of the second angled cut 460 can comprise a curved or radiused portion. The second angled cut 460 depicted herein includes a radius of approximately R 0.040. In the embodiment of FIG. 3A, the overall axial length of the skive with respect to the first section 420, the axial cut 440, and the second angled cut 460 can range from approximately 100 mm to 200 mm. Additional dimensions of the skive are contemplated herein and not limitation.

The catheter 100 further includes a midshaft section. As embodied herein and as illustrated in FIG. 2, the midshaft section of the catheter 100 includes a tubular midshaft member 520. The midshaft member 520 includes a guidewire lumen 210 and an inflation lumen 201 defined therethrough. The inflation lumen 201 of the midshaft member is in fluid communication with the inflation lumen 200 of the hypotube 220. Furthermore, at least a portion of the distal section of the hypotube 220 is disposed within the inflation lumen 201 of the midshaft member 520 with the inflation lumen 200 of the hypotube in fluid communication with the inflation lumen 201 of the midshaft member. The inflation lumen 201 of the midshaft member depicted herein comprises a generally crescent configuration at a proximal section thereof and the hypotube 220 is inserted into the inflation lumen 201, as further discussed herein.

As embodied herein and as illustrated in FIG. 2, an exterior surface of the midshaft member 520 can define a proximal port 280. The proximal port 280 is spaced distally from the proximal end of the catheter 100. The proximal port 280 is configured to receive a guidewire 260 therethrough and is in communication with the guidewire lumen 210 of the midshaft member 520. In one embodiment, the proximal port 280 is reinforced by the distal section of the hypotube and the distal section of the hypotube is disposed proximate the proximal port of the midshaft member 520. In another embodiment, at least a portion of the axial cut 440 is disposed proximate to the proximal port 280 of the guidewire lumen 210. The location of the proximal port 280 can depend upon various factors, such as the size of the balloon, as further discussed herein.

Figure 4:
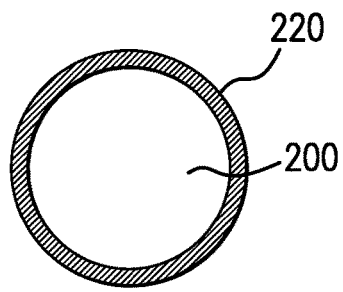
FIGS. 4, 5, 6, 7 are transverse cross sectional schematic views of the balloon catheter shown in FIG. 2, taken along lines 4-4, 5-5, 6-6, and 7-7, respectively.
Figure 5:
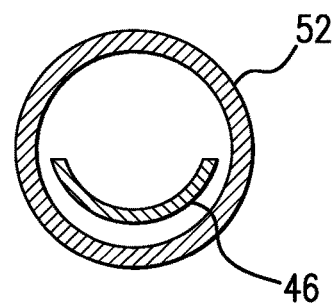

FIG. 4 is a cross-section of the catheter 100 of FIG. 2 along the lines 4-4. As depicted in FIG. 4, the hypotube 220 at this section is a single lumen member defining the inflation lumen 201 therethrough with a circular cross section. FIG. 5 is a cross-section of the catheter 100 of FIG. 2 along the lines 5-5. In FIG. 5, the inflation lumen 201 of the midshaft member 520 includes a substantially circular cross section. The inflation lumen 200 of the hypotube 220 is fluidly connected to the lumen 201 of the midshaft member 520. As depicted in FIG. 5, the second angled cut 460 is disposed within the lumen 201 of the midshaft member 520, as further discussed herein.

Figure 6:
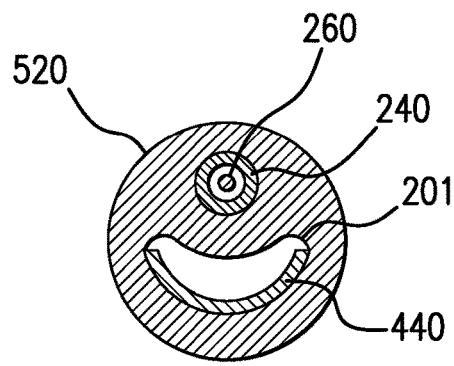

FIG. 6 is a cross-section of the catheter 100 of FIG. 2 along the lines 6-6. The midshaft member 520 at 6-6 includes a crescent like cross section for the inflation lumen 201. With respect to FIGS. 5 and 6, the lumen 201 of the midshaft member 520 transitions from a circular cross section at FIG. 5 to a crescent like cross section at FIG. 6. The transition of the circular cross section of the midshaft member 520 to the crescent like cross section of the midshaft member 520 allows for a smooth transition in flow, as described further herein.

At the cross section of FIG. 6, the axial cut 440 is disposed at least partially in the crescent inflation lumen 201 and is further discussed below. The space above the axial cut 440 defines the volume for inflation fluid flow. The corners of the crescent or "smiley" configuration can be rounded or otherwise provided in a suitable shape.

Figure 7:
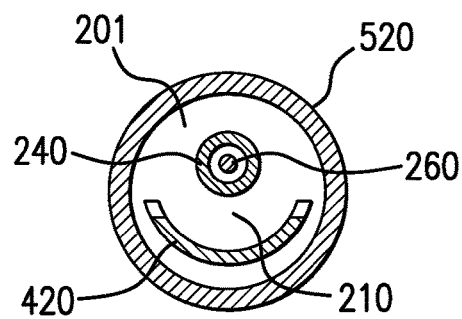

FIG. 7 is a cross-section of the catheter 100 of FIG. 2 along the lines 7-7. FIG. 7 depicts a cross section of the midshaft member 520 in which the inflation lumen 201 has transitioned from the crescent configuration to an annular configuration. The first angled cut 420 interfaces with the midshaft member 520 and is positioned adjacent, below as depicted in FIG. 7, the guidewire lumen 210 as defined by tubular member 240. The inflation lumen 201 is generally coaxial with the guidewire lumen 210. As depicted FIG. 2, the first angled cut 420 can extend distally beyond the midshaft member 520 into the distal tubular member 230, as further discussed herein.

At the cross section of the midshaft member 520 of FIG. 7, inflation lumen 201 and the guidewire lumen 210 each has a circular cross-section. Thus, as embodied herein and as shown in FIGS. 4-7, the inflation lumen 200 of the hypotube 220 transitions from a circular cross section at section 4-4 of FIG. 2, to a generally crescent or "smiley" configuration at section 7-7 of the inflation lumen 201 of the midshaft member 520 and then ultimately to a dual lumen coaxial arrangement at section 7-7. However, the inflation lumen 201 and the guidewire lumen 210 can have an alternative cross-sectional shape as desired.

The skive serves as a male end section of the hypotube 220 and the inflation lumen 200 of the midshaft member 520 serves as the female receiving end section. At least a portion of the stepped skive at the distal end section of the hypotube is configured to be received within the inflation lumen 201 of the midshaft member 520. The hypotube 220 is disposed within the crescent or smiley shaped inflation lumen to fluidly connect the inflation lumen 200 of the hypotube with the inflation lumen 201 of the midshaft member 520. For example, and as embodied herein the skive portion of the hypotube 220 is disposed within the inflation lumen 201 of the midshaft member 520, as depicted in FIGS. 1 and 6. The axial cut 440 interfaces with a portion of a surface of the inflation lumen 201 of the midshaft member 520 and at least the axial cut 440 can be press fit with the inflation lumen 201 of the midshaft member 520. The axial cut 440 is likewise partially disposed within the inflation lumen 201. Furthermore, as embodied herein, the first angled cut 420 is inserted through the inflation lumen 201 of the midshaft section and into the distal shaft section, as depicted in FIG. 2 and further discussed herein. Accordingly, the skive assists in joining and reinforcing the hypotube 220 with the midshaft member 520, while facilitating a smooth transition in flexibility.

The hypotube 220 can be bonded along the length of the hypotube or at portions along the length of the hypotube with the midshaft member 520, as depicted in FIG. 2. The distal section of the hypotube can have a roughened outer surface to enhance the bond therebetween. The hypotube 220 is concentrically aligned with the midshaft member 520. Accordingly, the outer diameter of the hypotube 220 is sized to fit concentrically within the midshaft member 520 at least at a distal section of the hypotube 220.

Furthermore, the hypotube 220 can be bonded with the midshaft member 520 along a portion of a length of the hypotube 220. Accordingly, an exterior surface of the hypotube 220 concentrically engages with an interior surface of the midshaft member 520 in the midshaft section. The skive couples the hypotube 220 with the midshaft member 520 and is further discussed below.

Turning back to FIG. 2, the distal shaft section of the catheter 100 further includes a distal tubular shaft member 230 extending distally from the midshaft member 520. The distal tubular shaft member 230 is coupled the hypotube 220 by the midshaft member 520. The distal tubular shaft member 230 is coupled to the midshaft member 530 by at least one of bonding, adhesive, lap joint, and butt joint or by other suitable configurations as known in the art.

As depicted herein, the distal tubular shaft member 230 has a guidewire lumen 211 and an inflation lumen 202 defined therein. The guidewire lumen 211 of the distal tubular shaft member 230 is in fluid communication with the guidewire lumen 210 of the midshaft member 520. The inflation lumen 202 of the distal tubular shaft member 230 is in fluid communication with the inflation lumen 201 of the midshaft member.

As embodied in FIG. 2, the distal tubular shaft member 230 includes an outer tubular member 231 extending from the midshaft member 520. The guidewire lumen 211 is defined by tubular member 240 extending from the midshaft member 520 through the outer tubular member 231 of the distal tubular shaft member 230. The outer tubular member 231 and the inner tubular member 240 define the inflation lumen 202 of the distal tubular shaft member 230 therebetween in fluid communication with the inflation lumen 201 of the midshaft member 520. Thus, distal tubular shaft member 230 can comprise a coaxial annular configuration with the inner tubular member 240 positioned within the outer tubular member 231. Alternatively, the distal tubular shaft member can be formed as a dual lumen monolithic member with the guidewire lumen and the inflation lumen defined therein if preferred.

FIG. 8 is a cross-section of the catheter 100 of FIG. 2 along the lines 8-8. As depicted in FIGS. 1 and 8, the inflation lumen 202 of the distal tubular shaft member 230 includes an annular configuration. The inflation lumen 202 is defined by the annular space between the interior surface of the outer tubular member 231 and the exterior surface of the inner tubular member 240, although a variety of suitable shaft configurations can alternatively be used including non-coaxial and multi-lumen extrusions. The transition from the circular to crescent to annular shape of the inflation lumen 200, 201, 202 allows for smooth flow without significant back pressure or resistance.

The inner tubular member 240 defines the guidewire lumen 210, 211 configured to slidably receive a guidewire 260 therein. The inner tubular member 240 can comprise one tube or be comprised of a plurality of tubes connected together. The inner tubular member 240 can be the same member extending through the midshaft member 520, or can be a separate member connected therein. Such configurations are known. An exterior surface of the outer tubular member 231 interfaces with an interior surface of the midshaft member 520 at a distal end section of the midshaft member 520. The midshaft member 520 and the outer tubular member 231 can be coupled in a variety of ways including, but not limited to bonding, adhesives, lap joints, butt joints and the like. The inflation lumen 201 of the midshaft member 520 is fluidly coupled to the inflation lumen 202 of the distal tubular shaft member 230 to provide for a path for inflation of the balloon, as further discussed herein.

Thus, from the proximal end section to the distal end section, the catheter 100 embodied herein transitions from a single lumen (inflation lumen) configuration in the proximal shaft section to a coaxial dual lumen (inflation lumen and guidewire lumen) configuration in the distal shaft section. The midshaft section generally defines the juncture between the single lumen hypotube and the dual lumen distal shaft section.

As depicted in FIG. 1, a balloon 140 is coupled to the distal tubular shaft member 230 and is in fluid communication with the inflation lumens 200, 201, and 202. FIG. 9 is a cross-section of the catheter 100 of FIG. 1 along the lines 9-9. As depicted in FIG. 9, a balloon 140 is sealingly secured to the distal tubular shaft member 230 such that an interior of the balloon is in fluid communication inflation lumens 200, 201, and 202.

For example, and turning back to FIG. 1, the balloon 140 has a proximal skirt section bonded to a distal end section of outer tubular member 231 and a distal skirt section bonded to a distal end section of inner tubular member 240.

Additional features proximate the balloon can include markers, stents, and an atramatic tip (not shown). Examples of such features and additional features include those described in U.S. Pat. No. 7,862,541; application Ser. No. 12/983,504; U.S. Pat. No. 7,549,975; U.S. patent application Ser. No. 12/468,745; U.S. Pat. No. 6,964,750; U.S. application Ser. No. 11/455,382; U.S. Pat. Nos. 7,833,597; 7,322,959; 7,303,798; U.S. application Ser. No. 11/775,480; U.S. application Ser. No. 12/945,566; U.S. Publication 2010/0285085; U.S. Publication 2010/0189876; and U.S. patent application Ser. No. 11/241,936; the contents of which are herein incorporated by reference in their entirety.

As depicted in FIG. 1, an adapter is provided at the proximal end of the catheter for access to the inflation lumen 200, 201, 202 collectively, and is configured for connecting to an inflation fluid source (not shown). The balloon 140 is provided at a distal end of the catheter and in fluid communication with the inflation lumen 200, 201, 202. The distal end of the catheter can be advanced to a desired region of a body lumen in a conventional manner and balloon 140 inflated to perform a medical procedure, such as dilate a stenosis and/or deliver a stent or the like. The catheter 100 is then withdrawn or repositioned for another procedure. FIG. 1 illustrates the balloon inflated.

The catheter can comprise a variety of suitable materials. In particular, the hypotube can be a more rigid material than the material of the midshaft member or the distal tubular shaft member. For example, the hypotube is typically a relatively high stiffness material such as a metal, such as but not limited to stainless steel, although a high durometer polymer can be used. In contrast, the midshaft member coupled to the hypotube can have more flexibility and can comprise a more flexible material. In one embodiment, the midshaft member comprises nylon 12 or other suitable polymeric material.

The distal shaft section can be more flexible than the proximal shaft section. For example, but not limitation, the outer tubular member can be a single or multi-layer member made of one or more polymers, such as different durometers of polyamide. Similarly, the inner tubular member can be a single or multi-layer member made of one or more polymeric materials. For example, in one embodiment, the inner tubular member is made of a trilayer with PEBAX 72D, Primacore, and HDPE for the outside, intermediary, and inside layers, respectively and discussed further herein. The distal shaft section can be distal blown as further discussed herein. Furthermore, the dual lumen configuration of the distal tubular shaft member can be constructed by a number of different techniques. For example, and as described further below and depicted herein, the combination of the midshaft member and the inner tubular member of the guidewire lumen can be melted within a shrink wrap, with a crescent shape mandrel therein to define the crescent or "smiley" shaped inflation lumen.

In accordance with another aspect of the disclosed subject matter, the distal shaft section can be formed of a tubular member or hypotube free of any outer coating, so as to have a bare exposed outer surface. In this manner, a hypotube of larger cross section can be used without jeopardizing the profile of the proximal shaft section as compared to a conventional rapid exchange catheter with a coated hypotube. For example, the reduction in thickness by omitting a coating can allow for a proportional increase in both the outer diameter and thus the inner diameter of the tubular member. Thus, the overall profile of the catheter along the proximal end section can remain the same, but the dimensions of the inflation lumen therein are increased. The increase in inner diameter can result in greater fluid flow for increased inflation or deflation as described. In some embodiments, the flow rate through the tubular member can increase the flow rate by 4 times as compared to catheters with coating having the same overall profile. Further, the bare hypotube can also result in a better grip and a reduction in kinking. When heated to the appropriate temperature, the midshaft member can be bonded directly to the hypotube. The textured surface at the hypotube can assist the adhesion of the midshaft member to the hypotube by increasing the surface area at the skive.

As embodied herein, and in accordance with another aspect, the juncture of the midshaft member can be formed as follows. The guidewire lumen can be formed by connecting an inner tubular member 240 to a tubular midshaft member at a side opening, which is created in the wall of the tubular midshaft member to define the proximal port 280. The tubular midshaft member is heated and attached with the inner tubular member within the interior of the midshaft member at the side opening. A mandrel or pressurizing fluid is provided within the guidewire lumen during the fusion, if desired or needed to maintain the guidewire lumen open. The crescent inflation lumen of the midshaft member is formed during the heating process by positioning a crescent shaped mandrel proximate the juncture of the inner tubular member with the tubular midshaft member. The heating process includes a temperature sufficient to soften or melt the materials of the tubular midshaft member to define the lumens therein. Shrink wrap material can be used to maintain the outer shape and dimension of the midshaft member by the fusion process. The mandrel and shrink wrap are then removed after the fusion or heating process is complete.

FIGS. 10A and 10B depict images of cross-sections of the midshaft section during manufacture. FIG. 10A depicts the cross section of the midshaft member 520 and inner tubular member 240 of a coaxial configuration, where the guidewire lumen 210 is concentric with the inflation lumen 201, similar to FIG. 8. FIG. 10B depicts a cross-section from the midshaft member after the melting or fusion process depicting the inflation lumen defined by a crescent mandrel. The dual lumen configuration of FIG. 10B can be formed by a number of other techniques. For example, the midshaft member can further include a dual lumen member extending at least a length thereof for purpose of strength and transition from the proximal end section to the distal end section.

In accordance with the disclosed subject matter, at least a portion of the catheter shaft 110 can comprise a tubular member formed of a biaxially oriented thermoplastic polymeric material, which in the illustrated embodiment can be the distal tubular shaft member 230 (hereafter "the biaxially oriented distal tubular shaft member") having the inflation lumen 202 therein. A catheter of the disclosed subject matter can have a biaxially oriented tubular member alternatively or additionally forming other sections of the catheter shaft including the proximal and midshaft sections. However, unlike the proximal shaft section, which is typically formed of a relatively-high bending stiffness material to provide sufficient push (force transmission) for advancing the catheter in the vasculature, the distal shaft section can have tubular members with increased flexibility to track over a guidewire in the tortuous vasculature or the like.

The polymeric material of the biaxially oriented distal tubular shaft member is biaxially oriented by radially and longitudinally expanding an extruded tube used to form the distal tubular shaft member. For example, the biaxially oriented distal tubular shaft member can be formed of a relatively soft/low durometer polymeric material. The polymer can have a Shore durometer hardness of not greater than about 55D to about 72D. A variety of suitable nonporous polymeric materials can be used including polyether block amide (PEBAX) copolymers, polyurethanes, polyethylenes, and polyesters. The polymeric material can have various levels of crystallinity, and thus can be crystalline or noncrystalline. In an embodiment, the polymer is a single polymer or copolymer (i.e., not a blend of two separate polymers). For example, the polymer can be PEBAX 63D, which has a Shore durometer hardness of about 63D.

In one embodiment, the distal tubular shaft member is a single-layered tubular member formed of the biaxially oriented polymer tubing. However, in other embodiments, the outer tubular member can be a multilayer configuration. The multilayer construction can, for example, include different durometers of polyamide. Examples and further disclosure of biaxially oriented tubular shaft members are provided in U.S. Pat. No. 7,906,066, which is incorporated in its entirety herein.

In the illustrated embodiment of FIG. 1, the biaxially oriented distal tubular shaft member 230 has a uniform outer diameter along the entire length of the distal tubular shaft member 230. For example, and with reference to a coronary dilation catheter, the biaxially oriented distal tubular shaft member has an inner diameter of about 0.020 to about 0.040 inches, and an outer diameter of about 0.0225 to about 0.0435 inches along at least a section thereof. The length of the biaxially oriented distal tubular shaft member 230 herein is between about 10 to about 25 cm.

It is desired for the rupture strength of the catheter shaft to be greater than that of the balloon. In the catheter of the disclosed subject matter, the balloon rated burst pressure is significantly less than (e.g., about 4 atm less than, or about 20% less than) that of the biaxially oriented tubular outer member.

Figure 11:
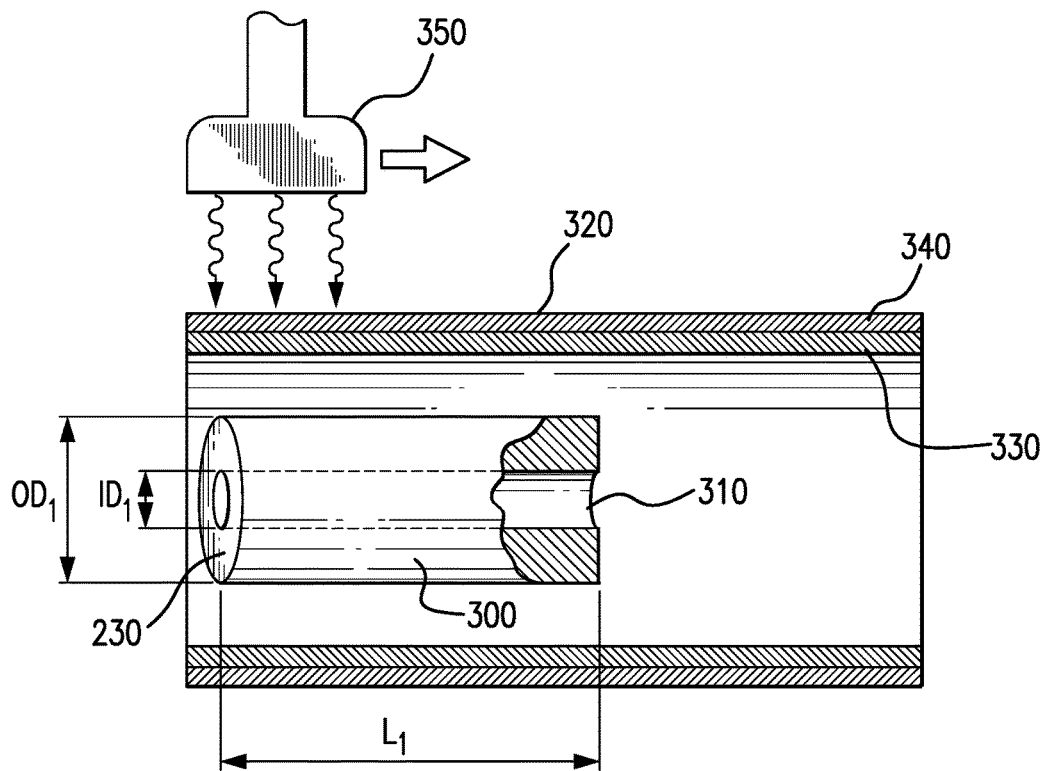
FIG. 11 illustrates the formation of the catheter shaft outer tubular member, in which an extruded tube is radially and longitudinally expanded in a capture member in a method embodying features of the disclosed subject matter, with the extruded tube shown prior to being radially and longitudinally expanded.
Figure 12:
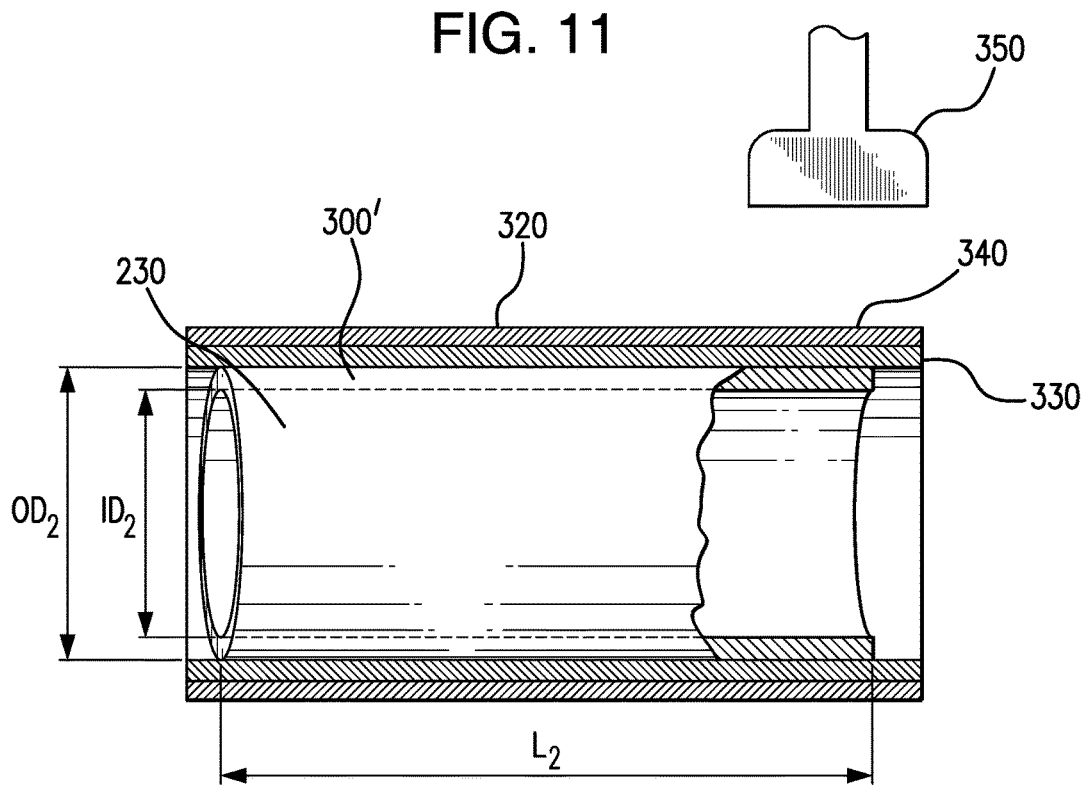
FIG. 12 illustrates the extruded tube of FIG. 11 after being radially and longitudinally expanded in the capture member.

FIGS. 11 and 12 illustrate a method of making a biaxially oriented tubular member such as the biaxially oriented distal tubular shaft member 230 of the catheter 100 of FIG. 1. A method of the disclosed subject matter generally comprises melt-extruding a thermoplastic polymeric material having a relatively low Shore durometer hardness, to form a tube 300 having a lumen 310, a first inner and outer diameter ($ID_1$, $OD_1$) and a first length ($L_1$), and cooling the extruded tube 300 to a temperature (e.g., to room temperature) which is less than an elevated temperature of the melt-extrusion. The cooled extruded tube 300 is placed within a capture member 320, heated to an elevated temperature, and radially and axially expanded in the capture member 320 to a second inner and outer diameter ($ID_2$, $OD_2$) and length ($L_2$), to thereby biaxially orient the polymeric material of the extruded tube 300. FIG. 11 illustrates the extruded tube 300 disposed within the capture member 320 prior to being expanded therein, and FIG. 12 illustrates the expanded tube 300' within the capture member 320 (i.e., the extruded tube 300 of FIG. 11 after being radially and longitudinally expanded within the capture member 320). After being radially and longitudinally expanded, the resulting expanded tube 300' is cooled to room temperature and heat stabilized as discussed in more detail below. The catheter is subsequently assembled, at least by sealingly securing a balloon to a distal end of the expanded tubular member such that the balloon has an interior in fluid communication with the expanded tubular member lumen.

In the embodiment of FIG. 11, the capture member 320 is tubular with an inner surface layer 330 of a lubricious polymeric material such as polytetrafluoroethylene (PTFE) for subsequent ease of part removal, reinforced with an outer high strength jacket layer 340 such as stainless steel tubing configured to prevent or inhibit diameter creep (growth) after repeated use. Thus, the capture member 320 is configured to radially restrain the growing tube 300, without the inner or outer diameter of the capture member 320 increasing at the elevated internal pressures used to radially expand the extruded tube 300.

The extruded tube 300 is heated to the elevated temperature within the capture member 320, which in the illustrated embodiment comprises directing heat from a heating nozzle 350 at the outer surface of the capture member 320. In an embodiment, the heating nozzle 350 traverses along a length of the extruded tube 300, from a first end to the opposite end. Thus, the radial and longitudinal expansion is initiated with only the first end of the extruded tube 300 heated by the nozzle 350 in one embodiment. In an embodiment, the extruded tube 300 is heated to an expansion elevated temperature which is less than the melt-extrusion elevated temperature (i.e., less than a melting temperature of the polymeric material).

The extruded tube 300 is axially expanded with a load applied on at least one end of the tube, e.g., using a vertical necking apparatus (not illustrated), and is radially expanded with pressurized media introduced into the extruded tube lumen from a pressurized media source (not illustrated) connected to one end of the extruded tube 300. Specifically, with the heating nozzle 350 heating the first end of the extruded tube 300, the heating nozzle 350 is moved toward the second end and the load is applied to the second end in the same direction as the heating nozzle movement to axially expand (i.e., stretch lengthwise) the extruded tube 300. The amount of the load required to provide the desired stretch percent depends on factors such as the tensile elongation, dimensions, material of the tubing 300, pressure of the pressurized media, and the expanded inner diameter. The pressurized media, e.g., compressed air, is at an elevated pressure sufficient to initiate the radial expansion, such that the wall hoop stress exceeds the material resistance (typically the yield stress) to stretching at the blowing temperature. The internal pressure used to radially expand the tubing 300 is typically about 400 to about 600 psi.

The extruded tube 300 can be simultaneously radially and axially expanded at the elevated temperature, for ease of manufacture. However, it can alternatively be sequentially expanded (i.e., first radially then longitudinally, or first longitudinally and then radially).

The tubing 300 can be radially expanded into contact with the inner surface of the capture member 310, to the second outer diameter which is about equal to the inner diameter of the capture member 310. The tubing 300 radially expands in all directions around the tubing circumference, resulting in circumferential orientation of the polymeric material. In an embodiment, the second inner diameter ($ID_2$) is at least about 5 times larger than the first inner diameter ($ID_1$) of the extruded tube (i.e., the blow-up-ratio, BUR, of the expanded tubular member 300' is at least about 5, and is more specifically about 5.8 to about 6). The large BUR provides a high degree of circumferential orientation, for a large increase in the rupture pressure of the tubing. In one embodiment, the tubing is radially expanded to substantially the maximum amount possible (i.e., to a BUR which is at least about 80% of the maximum BUR possible). Further embodiments and examples of making a balloon catheter shaft having high strength and flexibility can be found in U.S. Pat. No. 7,906,066 entitled "Method of making a balloon catheter shaft having high strength and flexibility," the contents of which is incorporated by reference herein in its entirety.

Although illustrated as a rapid exchange type balloon dilatation catheter, it should be understood that a biaxially oriented shaft tubular member of the disclosed subject matter can be used in a variety of catheters and catheter shaft configurations, including stent delivery balloon catheters and non-rapid exchange type catheters. For example, in one embodiment of an over-the-wire type catheter having a full length guidewire lumen which extends from the proximal to the distal end of the catheter, a biaxially oriented shaft outer tubular member would typically be provided along the distal shaft section (e.g., with a proximal end distally spaced from the proximal end of the catheter and a distal end at the balloon).

In another embodiment, the balloon can be formed of a polymeric material which is compatible with the material forming the outer surface of the shaft, to allow for fusion bonding, although the balloon can alternatively or additionally be adhesively bonded to the shaft. The balloon can be a relatively high rupture pressure, non-compliant balloon, which in one embodiment has a rupture pressure of about 20 to about 30 atm, such that the balloon can be inflated in the patient during a procedure at relatively high working pressure of about 180 atm. In one embodiment, the balloon has a rated burst pressure of about 14 to about 25 atm. The rated burst pressure (RBP), calculated from the average rupture pressure, is the pressure at which 99.9% of the balloons can be pressurized to without rupturing, with 95% confidence. Generally, a balloon is inflated in the patient during a procedure at working pressure of about 8 to about 180 atm.

In the embodiment as depicted in FIG. 1, the balloon 140 is depicted as a single layer balloon. However, multilayered balloons are contemplated herein. An example of a multilayered balloon for a catheter is described in U.S. Pat. No. 7,828,766 and U.S. application Ser. No. 12/897,202, the contents of which are herein incorporated by reference in their entirety. Further, various embodiments of catheters with other balloon configurations are described in U.S. Pat. No. 6,923,822; U.S. application Ser. No. 11/189,536; U.S. Publication Nos. 2009/0036829 and 2007/0021772, the contents of which are herein incorporated by reference in their entirety.

While the present disclosed subject matter is described herein in terms of certain embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

It will be understood that the above description of the present disclosed subject matter is susceptible to various modifications, changes and adaptations, and the same are intended to be comprehended within the meaning and range of equivalents of the appended claims.

What is claimed is:

1. A catheter comprising:
a hypotube having a proximal section and a distal section with an inflation lumen and a longitudinal axis defined therethrough, the distal section having a skive defined by a first angled cut, an axial cut, and a second angled cut, wherein the first angled cut extends at a first angle relative the longitudinal axis that is not perpendicular thereto, the second angled cut extends at a second angle relative the longitudinal axis that is not perpendicular thereto, and the axial cut is substantially parallel to the longitudinal axis;
a distal shaft portion including a guidewire lumen and an inflation lumen defined therethrough, the inflation lumen of the distal shaft portion in fluid communication with the inflation lumen of the hypotube, the inflation lumen of the distal shaft portion configured to receive at least a portion of the distal section of the hypotube; and
a balloon coupled to the distal shaft portion and in fluid communication with the inflation lumen of the distal shaft portion.

2. The catheter according to claim 1, wherein at least a portion of the distal section of the hypotube is disposed within the inflation lumen of the distal shaft portion, with the inflation lumen of the hypotube in fluid communication with the inflation lumen of the distal shaft portion.

3. The catheter according to claim 1, wherein the inflation lumen of the hypotube comprises a substantially circular cross-section.

4. The catheter according to claim 1, wherein the hypotube is bonded with the distal shaft portion along a portion of a length of the hypotube.

5. The catheter according to claim 4, wherein the distal section of the hypotube has a roughened outer surface.

6. The catheter according to claim 1, wherein the hypotube is made of a material more rigid than a material of the distal shaft portion.

7. The catheter according to claim 6, wherein the material of the hypotube comprises at least one of metal or high durometer polymer.

8. The catheter according to claim 1, wherein the hypotube has a wall thickness of between about 0.0030 inches and about 0.0090 inches.

9. The catheter according to claim 1, wherein the hypotube reduces in cross-sectional dimension distally along the skive.

10. The catheter according to claim 1, wherein the axial cut is disposed between the first angled cut and the second angled cut.

11. The catheter according to claim 1, wherein the first angled cut and the second angled cut comprise at least one of a linear angled configuration or a curved configuration.

12. The catheter according to claim 1, wherein the first angled cut and the second angled cut are substantially parallel with each other.

13. The catheter according to claim 1, wherein the first angle is different from the second angle.

14. The catheter according to claim 1, wherein at least the axial cut interfaces with a portion of a surface of the inflation lumen of the distal shaft portion.

15. The catheter according to claim 1, wherein at least axial cut is press fit with the inflation lumen of the distal shaft portion.

16. The catheter according to claim 1, wherein the first angled cut has an axial length between approximately 20 mm to approximately 30 mm.

17. The catheter according to claim 1, wherein the first angled cut has an overall height when measured from a side of between about 5% to approximately 25% of a diameter of the hypotube.

18. The catheter according to claim 1, wherein the axial cut has an overall height when measured from a side of between about 20% to approximately 50% of a diameter of the hypotube.

19. The catheter according to claim 1, wherein the axial cut has an axial length of approximately 10 mm to approximately 40 mm.

20. The catheter according to claim 1, wherein the second angled cut has an overall height when measured from a side of between about 50% to approximately 100% of a diameter of the hypotube.

21. The catheter according to claim 1, wherein a proximal end of the second angled cut comprises a radiused portion.

22. The catheter according to claim 1, wherein the skive has an overall axial length of between approximately 100 mm to approximately 200 mm.

23. The catheter according to claim 1, wherein an exterior surface of the distal shaft portion defines a proximal port to receive a guidewire therethrough, the proximal port in communication with the guidewire lumen of the distal shaft portion.

24. The catheter according to claim 23, wherein the distal section of the hypotube is disposed proximate the proximal port of the distal shaft portion.

25. The catheter according to claim 1, wherein the inflation lumen of the distal shaft portion comprises a generally crescent configuration.

26. The catheter according to claim 1, wherein the distal shaft portion comprises nylon 12.

27. The catheter according to claim 1, wherein the distal shaft portion comprises:
   an inner tubular member and having the guidewire lumen of the distal shaft portion defined therein, and
   an outer tubular member with the inner tubular member disposed therein, the outer tubular member and the inner tubular member defining an inflation lumen of the distal shaft portion therebetween.

28. The catheter according to claim 1, wherein the distal shaft portion comprises at least one of a multilayer construction with different durometers of polyamide or a single-layered tubular member construction.

29. The catheter according to claim 1, wherein the distal shaft portion comprises a biaxially oriented thermoplastic polymeric material.

30. The catheter according to claim 1, wherein the distal section of the hypotube has a bare exposed outer surface and the distal shaft portion is directly bonded to the bare exposed outer surface of the hypotube along a portion of the length of the hypotube.

31. A method of making a catheter comprising:
   providing a hypotube having a proximal section and a distal section with an inflation lumen and a longitudinal axis defined therethrough, the distal section having a skive defined by a first angled cut, an axial cut, and a second angled cut, wherein the first angled cut extends at a first angle relative the longitudinal axis that is not perpendicular thereto, the second angled cut extends at a second angle relative the longitudinal axis that is not perpendicular thereto, the axial cut is substantially parallel to the longitudinal axis, the first angled cut extends to a distal end of the hypotube, and the distal end of the hypotube comprises a blunt end;
   forming a distal shaft portion including a guidewire lumen and an inflation lumen defined therethrough, the inflation lumen of the distal shaft portion configured to receive at least a portion of the distal section of the hypotube;
   inserting the distal section of the hypotube within the distal shaft portion with at least the axial cut of the skive engaging the inflation lumen of the distal shaft portion and the inflation lumen of the distal shaft portion in fluid communication with the inflation lumen of the hypotube; and
   bonding the distal shaft portion to an outer surface of the hypotube.

32. The method of claim 31, wherein forming the distal shaft portion comprises
   creating a proximal port in a wall of the distal shaft portion,
   coupling the inner tubular member to the distal shaft portion at the proximal port within an interior of the distal shaft portion,
   positioning a crescent shaped mandrel in the distal shaft portion adjacent the inner tubular member, and
   heating the distal shaft portion.

33. The method of claim 31, wherein the outer surface of the hypotube is roughened prior to bonding of the distal shaft portion thereto.

34. The method of claim 31, wherein forming the distal shaft portion comprises directly bonding the distal shaft portion to a bare exposed outer surface of the distal section of the hypotube along a portion of the length of the hypotube.

\* \* \* \* \*